United States Patent [19]

Vitobello et al.

[11] 4,376,167
[45] Mar. 8, 1983

[54] HYDROLYSIS OF RAFFINOSE BY ALPHA-GALACTOXIDASE

[75] Inventors: Vincenza Vitobello; Paolo Branduzzi; Nadia Cimini, all of Rome, Italy

[73] Assignee: E.N.I. Ente Nazionale Idrocarburi, Rome, Italy

[21] Appl. No.: 213,657

[22] Filed: Dec. 5, 1980

[30] Foreign Application Priority Data

Feb. 1, 1980 [IT] Italy ................................ 19618 A/80

[51] Int. Cl.$^3$ .......................... C13J 1/00; C12N 9/40; C12R 1/865
[52] U.S. Cl. .................................... 435/276; 435/208; 435/942
[58] Field of Search ................ 435/208, 276, 942, 940

[56] References Cited

PUBLICATIONS

Chemical Abstracts vol. 84: 103854v, (1976), Abstract of Japan Kokai 75 63,187, (Suzuki et al.).
Chemical Abstracts vol. 91: 73290h, (1979).
Chemical Abstracts vol. 93: 41179d, (1980).

*Primary Examiner*—Lionel M. Shapiro
*Attorney, Agent, or Firm*—Morgan, Finnegan, Pine, Foley & Lee

[57] ABSTRACT

The invention relates to a process for the production of the alpha-galactoxidase enzyme by culturing yeasts of the *Saccharomyces cerevisiae* genus in a temperature range from 20° C. to 40° C.

The invention also relates to a process for enzymic hydrolysis of raffinose by alpha-galactoxidase from *Saccharomyces cerevisiae*. Such hydrolysis may take place with the yeast cells being present or also in the presence of enzymic extracts, both as such and enriched. An important advantage of the invention is the high alpha-galactoxidasic activity of the selected microorganisms, together with the absence of any invertasic activity.

3 Claims, No Drawings

HYDROLYSIS OF RAFFINOSE BY ALPHA-GALACTOXIDASE

This invention relates to a process for the production of the alpha-galactoxidase enzyme (E.C. 3.2.1.2.2) by culturing microorganisms of the Saccharomyces genus and relates also to the hydrolysis of raffinose by employing such an enzyme.

Raffinose, a trisaccharide with occurs in significant amounts in sugar beets, hinders the crystallization of sucrose and thus the extraction yields are lowered. This fact is a serious economical problem for sugar mills, so that the hydrolysis of raffinose becomes a must so as to improve both the quality and the efficiency of the process of crystallization of the extracted sugar.

Many papers describe enzymic processes for hydrolyzing raffinose, which exploit enzymes extracted from a number of species of microorganisms of the genera Absidia, Aspergillus, Bacillus, Circinella, Escherichia, Micrococcus, Mortierella, Penicillium and others.

However, when culturing many microorganisms, the cellular extract contains not only alpha-galactoxidase but also invertase, so that, in the treatment of sugar beet molasses, the hydrolysis of raffinose is undesirably accompanied by the hydrolysis of sucrose.

The outstanding advantage of the present invention is that the microorganisms selected by the present Applicants and which belong to the Saccharomyces genus happily combine the advantage of a culturing time which is positively reduced over that of the moulds with the property of possessing a high alpha-galactoxidasic activity but no invertasic activity.

These microorganisms, which have been isolated from olive mill waste water in the Monterotondo (Rome, Italy) area, have been classified as *Saccharomyces cerevisiae, var. oleaceous* and *Saccharomyces cerevisiae, var. oleaginosus* and have duly been deposited with the Northern Regional Center of the U.S. Department of Agriculture, Peoria, Ill., where they have been allotted the respective numbers NRRL Y 12056 and NRRL Y 12057.

Their cultural, morphological and physiological characteristics are reported hereunder.

A-Cultural characteristics.
 1. Solid medium (3 days): Malt agar The colonies are buttery, cream colored and glossy.
 2. Liquid medium (3 days): Malt extract A sediment is formed (in the S.cerevisiae, var. oleaginosus a faint ring is observed).

B-Morphological characteristics.
 1. Characteristics of the vegetative cells: The cells are ellipsoidal, cylindrical and sometimes elongate.
 2. Formation of pseudomycelium or of true mycelium: A rudimentary pseudomycelium is present under anaerobic conditions.

C-Sexual characteristics:
The vegetative cells are directly converted into asci, which contain from one to four spheroidal spores.

D-Physiological characteristics:
 1. Utilization of carbon sources:
  (a) Fermentation:

|  | S. cerevisiae var. oleaceus | S. cerevisiae var. oleaginosus |
|---|---|---|
| Glucose | + | + |
| Galactose | − | + |
| Maltose | − | + |
| Threalose | − | − |
| Melibiose | + | + |
| Raffinose | − | + |

(b) Assimilation:

|  | S. cerevisiae var. oleaceus | S. cerevisiae var. oleaginosus |
|---|---|---|
| Glucose | + | + |
| Galactose | ± | + |
| Maltose | − | + |
| Threalose | ± | ± |
| Melibiose | + | + |
| Raffinose | ± | ± |
| D-mannitol | ± | − |
| D-glucitol | ± | − |
| Ethanol | ± | ± |
| Glycerol | ± | ± |
| DL-lactic acid | ± | − |

The other carbon compounds are not assimilated.
 2. Assimilation of nitrogeneous compounds: Potassium nitrate: negative
 3. Growth at 37° C.: positive For the classification, there has been followed the descripted scheme by J. P. Van der Walt in "The Yeasts", 2nd Edition, edited by J. Lodder.

The cultures of the strains which belong to this invention can be prepared under aerobic conditions by any known method, for example, in culturing surfaces, or preferably under submerged cultures using stirred fermentors.

A culturing medium, which can be either solid or liquid, contains a source of assimilable carbon, a source of nitrogen and mineral salts.

As carbon sources glucose, melibiose, raffinose and also other sugars, glycerol and sodium acetate can be used.

As nitrogen sources inorganic and organic nitrogen compounds, such as meat extract, yeast extract, peptone, triptone, aminoacids casein hydrolysates, soybean flour and ammonium salts can be used.

Another outstanding advantage deriving from the use of the microorganisms in question is the fact that the enzyme is produced when they are cultured on glucose (the enzyme is constitutive).

An appropriate culturing medium has, for example, the following composition:
 Yeast extract: 5–20 g/l (grams per liter)
 Glucose: 10 g/l
 Traces of $NaH_2PO_4$, $MgSO_4$, $(NH_4)_2SO_4$: 1 g/l The pH range for culturing is from 4 to 7 and is preferably from 5.0 to 5.5, the temperature is comprised between 20° C. and 40° C., preferably between 25° C. and 28° C.

The enzyme production can be boosted by the addition of small amounts of melibiose, which, as is known, is the disaccharide deriving from the partial hydrolysis of raffinose. Melibiose can directly be added to the culturing medium before the inoculum, or as the logarithmic growth stage is over. The induction time may vary from 16 hours to 72 hours and is preferably between 40 hours and 48 hours.

The cells collected during fermentation or on completion of same can be used as such or in dry powder form. As an alternative, raw or purified extracts of such cells may be used.

To this purpose, the cells are broken with any known method and the enzyme-containing raw or purified extract is used.

Lastly, a further technical and economical improvement can be achieved by immobilizing the enzyme by combining it with macromolecular compounds, by forming chemical bonds with the matrix, or by ionic bonding, or also by physical immobilization of the enzyme or of the cells.

The cells thus obtained are added, as such or immobilized, to a reaction mixture which contains molasses, at a pH ranging from 4 to 7 and at a temperature of from 30° C. to 60° C. The raffinose which is contained in molasses is thus hydrolyzed to galactose and sucrose, the yield of this latter being thus improved.

The following Examples illustrate other procedural hints for the present invention, but do not limit its scope.

EXAMPLE 1

A culturing broth is prepared, having the following composition:
$(NH_4)_2SO_4$: 5 g/l
$MgSO_4.7H_2O$: 5 g/l
$Na_2HPO_4.12H_2O$: 4.6 g/l
$KH_2PO_4$: 3 g/l
NaCl: 0.1 g/l
$CaCl_2$: 0.05 g/l
Yeast extract: 10 g/l
Melibiose: 10 g/l These compounds are dissolved in deionized water and acidifying to pH 3.5 with hydrochloric acid.

The thusly prepared culturing medium was distributed in broad-necked, 500-ml Erlenmayer flasks (100 mls of broth per flask, sterilization at 116° C. for 30 mins). The flasks were inoculated with 1 ml of a culture of the Saccharomyces cerevisiae, var.oleaceus strain in 250-ml flasks containing 50 mls of the same broth and growth was promoted at 25° C. during 16 hours with stirring (180 rpm).

The fermentation flasks were placed to incubation with stirring (180 rpm) at 25° C.

After 40 hours as from the inoculation, the cells of the broth cultures were collected by centrifuging and washed with phosphate buffer (0.1 M, pH 5.6). From 100 mls of culturing broth there was obtained 0.55 g of dried cells.

The moist cells collected from 100 ml of broth were reslurried in 100 ml of phosphate buffer (0.1 M, pH 5.6) and the enzymic activity was assayed. 1 g of dried cells contained about $1.10^7$ enzyme units. The enzymic activity was measured with the following procedure.

To 1 ml of buffered cell slurry there were added 4 mls of phosphate buffer (0.1 M, pH 5.6) and a few drops of toluene for rupturing the cell walls. After 15 mins. of incubation with stirring at 40° C., the slurry was supplemented with 10 ml of a 1% solution (wt/vol) of melibiose in phosphate buffer (0.1 M, pH 5.6).

The reaction was incubated at 40° C. for 2 hrs in a stirred water bath and was discontinued by boiling for 15 mins the samples taken from the reaction mixture.

The concentration of glucose, as produced by the hydrolysis of melibiose during the reaction was determined with the colorimetric GOD-Perid method by Boehringer Mannheim GmbH.

The optical density of the coloured samples was measured at room temperature in a Perkin-Elmer Coleman 55 spectrophotometer, optical path of the boat=0.1 dm (decimeter) at the wavelength of 436 millimicrons.

If one defines as one unit the quantity of enzyme which produces 1 microgram of glucose in 2 hrs under the assay conditions set forth above, the units of enzyme per gram of dried cells can be calculated with the following formula:

$$\frac{U}{\text{grams of dried cells}} = \frac{(E_{2h} - E_{0h}) \cdot 18.2 \cdot 15 \cdot 100}{E_{standard} \cdot C}$$

wherein:
$E_{2h}$ is the optical density of the sample taken after 2 hours
$E_{0h}$ is the optical density of the sample taken at zero hours.
$E_{standard}$ is the optical density of a standard solution of glucose, which contains 18.2 micrograms of glucose per milliliter
C is grams of dried cells in 100 ml of culturing broth.

EXAMPLE 2

A culturing broth was prepared, having the following composition:
$(NH_4)_2SO_4$: 5 g/l
$MgSO_4.7H_2O$: 0.5 g/l
$Na_2HPO_4.12H_2O$: 4.6 g/l
$KH_2PO_4$: 3 g/l
NaCl: 0.1 g/l
$CaCl_2$: 0.05 g/l
Yeast extract: 10 g/l
Glucose: 10 g/l The above listed compounds were dissolved in deionized water and the pH was then adjusted to 5.3 with hydrochloric acid.

Cultures in such broth of the strain Saccharomyces cerevisiae, var. oleaceus, prepared as set forth in EX. 1, were incubated with stirring (oribtal, 180 rpm) at 27° C.

39 hours as from the inoculation, the culturing broth cells were collected by centrifuging and washed with phosphate buffer (0.1 M, pH 5.6).

From 100 ml of culturing broth there was obtained 0.546 g of dried cells. The cells collected from 100 ml of broth were reslurried in 100 ml of phosphate buffer (0.1 M, pH 5.6) and assayed for the enzymic activity: 1 g of dried cells contained $9.4.10^6$ enzyme units.

EXAMPLE 3

A culturing medium was prepared, having the following composition:
$(NH_4)_2SO_4$: 5.00 g/l
$MgSO_4.7H_2O$: 0.5 g/l
$Na_2HPO_4.12H_2O$: 4.6 g/l
$KH_2PO_4$: 3.00 g/l
NaCl: 0.1 g/l
$CaCl_2$: 0.05 g/l
Yeast extract: 10 g/l
Glucose: 10 g/l
Melibiose: 1 g/l The above listed compounds were dissolved in deionized water and the pH was adjusted with hydrochloric acid to 5.3.

Cultures of the strain Saccharomyces cerevisiae, var. oleaceus, prepared as in EXAMPLE 1, were incubated with oribital stirring (180 rpm) at 27° C. 43 hours as from the inoculation, the cells from the broth cultures were collected by centrifuging and washed with phosphate buffer (0.1 M, pH 5.6). From 100 ml of broth culture there was obtained 0.594 g of dried cells.

The cells collected from 100 ml of culturing broth were reslurried in 100 ml of phosphate buffer (0.1 M, pH 5.6) and assayed for enzymic activity: 1 g of dried cells contained $1.6 \cdot 10^7$ enzyme units.

EXAMPLE 4

A culturing medium was prepared having the following composition:
$(NH_4)_2SO_4$: 5.00 g/l
$MgSO_4.7H_2O$: 0.05 g/l
$NaHPO_4.12H_2O$: 4.6 g/l
$KH_2PO_4$: 3.0 g/l
NaCl: 0.1 g/l
$CaCl_2$: 0.05 g/l
Yeast extract: 10.0 g/l
Glucose: 5.0 g/l
Melibiose: 5.0 g/l The above listed compounds were dissolved in deionized water and the pH was adjusted to 5.3 with hydrochloric acid.

Cultures of *Saccharomyces cerevisiae, var.oleaceus* in such a broth, prepared as in EXAMPLE 1, were incubated with orbital stirring (180 rpm) at 29° C. 48 hours as from the inoculation of the culturing broth the cells were collected by centrifuging and washed with phosphate buffer (0.1 M, pH 5.6). From 100 ml of culturing broth there was obtained 0.365 g of dried cells.

6 ml of culturing broth were added to 50 ml of 35° Brix molasses, containing 1.6% by wt of raffinose on the total solid matters, and were adjusted to a pH of 5.2 with $H_2SO_4$. The treatment was carried out at 40° C. with stirring for 16 hours. The concentration of galactose, a product of the hydrolysis of raffinose during the reaction, was determined with the method Lactose/-Galactose UV-Test by Boehringer Mannheim GmbH. Under the conditions set forth above there were produced 153 micromols of galactose, equivalent to the hydrolysis of the 30% of the totally present raffinose.

We claim:

1. The process of hydrolysing raffinose contained in a sucrose containing product comprising reacting said sucrose containing product with a microorganism selecting from the group consisting of *Saccharomyces cerevisiae, var. oleaceous* and *Saccharomyces cerevisiae var. oleaginosus*.

2. The process of claim 1 where said microorganism is in the form of whole cells or an alpha-galactoxidase containing extract.

3. The process of claim 1 wherein said sucrose containing product is selected from sugar beet and molasses.

* * * * *